US012807992B2

(12) United States Patent
Wu et al.

(10) Patent No.: US 12,807,992 B2
(45) Date of Patent: Nov. 24, 2026

(54) REAGENT FOR DETECTING EXPRESSION LEVEL OF HUMAN HISTAMINE RECEPTOR HRH4 mRNA, KIT AND DETECTION METHOD

(71) Applicant: HANGZHOU ZHEDA DIXUN BIOLOGICAL GENE ENGINEERING CO., LTD, Hangzhou (CN)

(72) Inventors: Shandong Wu, Hangzhou (CN); Yi Liu, Hangzhou (CN); Zhoujie Wu, Hangzhou (CN); Xuehan Jiang, Hangzhou (CN); Xukai Yang, Hangzhou (CN); Meijie Wang, Hangzhou (CN); Weiyue Cai, Hangzhou (CN)

(73) Assignee: HANGZHOU ZHEDA DIXUN BIOLOGICAL GENE ENGINEERING CO., LTD, Hangzhou (CN)

( * ) Notice: Subject to any disclaimer, the term of this patent is extended or adjusted under 35 U.S.C. 154(b) by 455 days.

(21) Appl. No.: 18/282,159

(22) PCT Filed: Aug. 4, 2021

(86) PCT No.: PCT/CN2021/110526
§ 371 (c)(1),
(2) Date: Sep. 14, 2023

(87) PCT Pub. No.: WO2023/010329
PCT Pub. Date: Feb. 9, 2023

(65) Prior Publication Data
US 2024/0150832 A1 May 9, 2024

(51) Int. Cl.
*C07H 21/04* (2006.01)
*C12Q 1/68* (2018.01)
*C12Q 1/6876* (2018.01)
*C12Q 1/686* (2018.01)

(52) U.S. Cl.
CPC .......... *C12Q 1/6876* (2013.01); *C12Q 1/686* (2013.01); *C12Q 2600/158* (2013.01)

(58) Field of Classification Search
None
See application file for complete search history.

(56) References Cited

U.S. PATENT DOCUMENTS 7,164,003 B2 * 1/2007 Gallagher ............ C07K 14/723
435/320.1

FOREIGN PATENT DOCUMENTS

| | | | |
|---|---|---|---|
| CN | 104195225 | A | 12/2014 |
| CN | 105017385 | A | 11/2015 |
| CN | 105671119 | A | 6/2016 |
| CN | 110592290 | A | 12/2019 |
| CN | 110694065 | A | 1/2020 |
| CN | 112877469 | A | 6/2021 |
| CN | 113584154 | A | 11/2021 |
| WO | 2001092485 | A1 | 12/2001 |

OTHER PUBLICATIONS

Fang et al. (BMC Cancer, vol. 11, No. 195, 2011) in view of Gallagher et al. (U.S. Pat. No. 7,164,003, Jan. 16, 2007) (Year: 2007).*

Nguyen et al. (Molecular Pharmacology, vol. 59, No. 3, pp. 427-433, 2001) (Year: 2001).*

Untergasser et al. (Primer3Plus, an enhanced web interface to Primer3, Nucleic Acids Research, 2007, vol. 35, 2007). (Year: 2007).*

NEB catalog (1998/1999), pp. 121, 284. (Year: 1998).*

Soltany-Rezaee-Rad (Biologicals, vol. 32, pp. 130-135, 2015) (Year: 2015).*

Tsybulsky et al. (Molecular and Cellular probes, vol. 30, pp. 2385-290, 2016). (Year: 2016).*

International Search Report and translation for PCT/CN2021/110526 dated May 9, 2022.

Li, ZiGang, The technical of biological detection, China Light Industry Press, p. 266, Aug. 31, 2016, Beijing, China.

Xiao, Jing, Modern medical inspection technology, Tianjin Science and Technology Press, Jan. 2018, p. 67, Tianjin, China.

Zhang C, et al. (2012) Deletion and Down-Regulation of HRH4 Gene in Gastric Carcinomas: A Potential Correlation with Tumor Progression. PLoS ONE 7(2): e31207. doi: 10.1371/journal.pone.0031207, Feb. 20, 2012.

* cited by examiner

*Primary Examiner* — Jeanine A Goldberg
(74) *Attorney, Agent, or Firm* — PORUS IP LLC

(57) ABSTRACT

The present disclosure provides a reagent for detecting an expression level of a human histamine receptor HRH4 mRNA, a kit and a detection method. In the present disclosure, the reagent includes a specific primer and a probe for a human histamine receptor HRH4, the specific primer includes an HRH4-F and an HRH4-R, and the probe includes an H4-Probe; and the HRH4-F has a nucleotide sequence shown in SEQ ID NO. 1, the HRH4-R has a nucleotide sequence shown in SEQ ID NO. 2 and the H4-Probe has a nucleotide sequence shown in SEQ ID NO. 3. In the present disclosure, a kit for one-step detection and a detection method based on the reagent are prepared, and the expression level of the HRH4 mRNA can be one-step quantitatively detected with simple operation and short detection time.

8 Claims, 9 Drawing Sheets

Specification includes a Sequence Listing.

REAGENT FOR DETECTING EXPRESSION LEVEL OF HUMAN HISTAMINE RECEPTOR HRH4 mRNA, KIT AND DETECTION METHOD

CROSS-REFERENCE TO RELATED APPLICATION

This application is a national stage application of International Patent Application No. PCT/CN2021/110526, filed on Aug. 4, 2021, which is incorporated by reference herein in its entirety.

REFERENCE TO SEQUENCE LISTING

A computer readable TXT file entitled "SEQUENCE LISTING", that was created on Jun. 26, 2026, with a file size of about 3022 bytes, contains the sequence listing for this application, has been filed with this application, and is hereby incorporated by reference in its entirety.

TECHNICAL FIELD

The present disclosure belongs to the technical field of biological detection, and specifically relates to a reagent for detecting an expression level of a human histamine receptor HRH4 mRNA, a kit and a detection method.

BACKGROUND

Histamine is an active amine compound widely present in animals and plants, is formed by the decarboxylation of a histidine, and is usually stored in the tissues. The histamine is an important chemical conductive substance in the body, can affect many cell reactions, including allergies, inflammatory reactions, and gastric acid secretion, etc. When the body is stimulated to trigger an antigen-antibody reaction, the cell membrane permeability of mast cells changes to release histamine, and the histamine interacts with a histamine receptor to produce pathophysiological effects. The synthesis of a histamine mainly occurs in mast cells, basophils, lungs, skin and gastrointestinal mucosa, and is consistent with the tissues that store the histamine. The histamine, like other transmitters, binds to specific receptors on target cells, thereby changing the biological activity of cells and exerting wide physiological or pathological effects. The inflammatory effect of histamine, namely the effect of histamine on the immune homeostasis in the body depends on the expression and activity of currently-known 4 histamine receptors. The 4 histamine receptors are named in the order of discovery: a histamine 1 (H1) receptor, a histamine 2 (H2) receptor, a histamine 3 (H3) receptor, and a histamine 4 (H4) receptor; where, the H4 receptor is predominantly distributed in the immune system or hematopoietic-related tissues or cells, and is highly expressed in bone marrow, peripheral hematopoietic cells and other sites related to inflammation. Therefore, the H4 receptor has become a new therapeutic target in immune diseases such as allergic reactions and asthma. The H4 receptor is involved in the chemotaxis of mast cells, eosinophils, and dendritic cells, as well as the production of cytokines in T cells and dendritic cells, and is involved in inflammatory reactions.

Most patients with allergic diseases use symptomatic treatment based on the experience of doctors and use antihistamines to relieve allergic symptoms. The antihistamines that target the H1 receptor are effective for some allergic patients, but still have limitations. H4 receptor antagonists can have a desirable therapeutic effect on patients that have ineffective treatment effect with H1 receptor antagonists. However, the treatment with antihistamines is not effective for all patients, and cannot quantify the therapeutic effect; and long-term medication will also produce a series of side effects. There are no relevant studies and records on this at present.

SUMMARY

In view of this, the present disclosure provides a reagent for detecting an expression level of a human histamine receptor HRH4 mRNA, a kit and a detection method. The expression level of the HRH4 mRNA can be detected using an RNA one-step method. The present disclosure provides a detection method with high accuracy, wide detection range and high sensitivity for the detection of HRH4 proteins.

In order to realize the above objective, the present disclosure provides the following technical solutions:

The present disclosure provides a reagent for detecting an expression level of a human histamine receptor HRH4 mRNA, including a specific primer and a probe for a human histamine receptor HRH4, where the specific primer includes an HRH4-F and an HRH4-R, and the probe includes an H4-Probe; and the HRH4-F has a nucleotide sequence shown in SEQ ID NO. 1, the HRH4-R has a nucleotide sequence shown in SEQ ID NO. 2 and the H4-Probe has a nucleotide sequence shown in SEQ ID NO. 3.

Preferably, the reagent may further include a specific primer and a probe of a reference gene GAPDH, where the specific primer of the GAPDH may include a GAPDH-F and a GAPDH-R, and the probe of the GAPDH may include a G-Probe; and the GAPDH-F may have a nucleotide sequence shown in SEQ ID NO. 4, the GAPDH-R may have a nucleotide sequence shown in SEQ ID NO. 5 and the G-Probe may have a nucleotide sequence shown in SEQ ID NO. ID NO. 6.

Preferably, 5'-ends of the H4-Probe and G-Probe may be separately labeled with different fluorescent reporter groups, and 3'-ends of the H4-Probe and G-Probe may be labeled with a same quenching group or different quenching groups.

Preferably, the fluorescent reporter group may include a 6-carboxyfluorescein (FAM) and a 2,7-dimethyl-4,5-dichloro-6-carboxyfluorescein (JOE), and the quenching group may include a Black Hole Quencher-1 (BHQ1).

Preferably, the HRH4-F, the HRH4-R, the H4-Probe, the GAPDH-F, the GAPDH-R and the G-Probe in the reagent may have a concentration of 2.25 nM, 1.5 nM, 1.5 nM, 1 nM, 1 nM and 1.5 nM, respectively.

The present disclosure further provides a kit for one-step detection of an expression level of a human histamine receptor HRH4 mRNA, including the reagent, a PCR reaction solution, an enzyme mixed solution, a carboxy-X-rhodamine (ROX) reference dye and nuclease-free water.

Preferably, the PCR reaction solution may include a deoxy-ribonucleoside triphosphate (dNTP) mix, MgCl and a buffer; and the enzyme mixed solution may include a *Thermus aquaticus* (Taq) enzyme, a reverse transcriptase, a ribonuclease (RNase) inhibitor and a Taq enzyme antibody with a mass ratio of 15:5:4:1.

Preferably, the kit may further include an RNA standard of the human histamine receptor HRH4.

The present disclosure further provides a method for detecting an expression level of a human histamine receptor HRH4 mRNA in one step based on the reagent or the kit, including the following steps: preparing a reaction system using an RNA standard of the human histamine receptor HRH4 as a template, conducting a quantitative real-time polymerase chain reaction (qRT-PCR), and constructing a standard curve using a logarithmic value of a copy number as an abscissa and using a Ct value as an ordinate;

preparing a same reaction system using an RNA extracted from a sample as a template, conducting a same qRT-PCR, and determining the expression level of the human histamine receptor HRH4 mRNA using the standard curve.

Preferably, the reaction system, calculated in 20 μL, may include: 2.4 μL of the nuclease-free water, 10 μL of the PCR reaction solution, 0.5 μL of the enzyme mixed solution, 0.5 μL of the ROX reference dye, 2 μL of the reagent and 5 μL of the template; and Preferably, a qRT-PCR program may include: 42° C. for 30 min; 95° C. for 1 min; 95° C. for 5 s, and 60° C. for 31 s, 40 cycles.

Preferably, the standard curve is $y=-3.177x+34.178$, $R^2=0.996$.

The present disclosure further provides use of the reagent or the kit as a basis in preparing a drug for treating an immune disease or as a tool in dynamically monitoring a therapeutic effect.

Compared with the prior art, the present disclosure has the beneficial effects as follows: the present disclosure provides a reagent for detecting an expression level of a human histamine receptor HRH4 mRNA, and a kit for one-step detection of the expression level of the HRH4 mRNA is prepared based on the reagent. The expression level of the HRH4 mRNA in human blood, nasal secretions, bronchial irrigating fluid, saliva, and tear samples can be one-step quantitatively detected using the reagent or the kit with simple operation and short detection time. The present disclosure provides a kit product that can guide the medication and accurately quantify the efficacy for H4 antihistamines.

In the present disclosure, the one-step detection is conducted based on the reagent and the kit without separate reverse transcription, which greatly reduces the risk of causing aerosol pollution. Compared with immunological detection methods, the detection method provided by the present disclosure has high sensitivity, can detect low-concentration clinical samples, can sensitively detect changes in HRH4 content, and has a detection range spanning at least 6 orders of magnitude. Accordingly, the accuracy of the detection results is increased, and at least 80 people can be detected within 1 hour, such that the treatment effect can be dynamically monitored and evaluated in an earlier, more accurate, and faster manner.

DETAILED DESCRIPTION OF THE INVENTION

Figure 1:
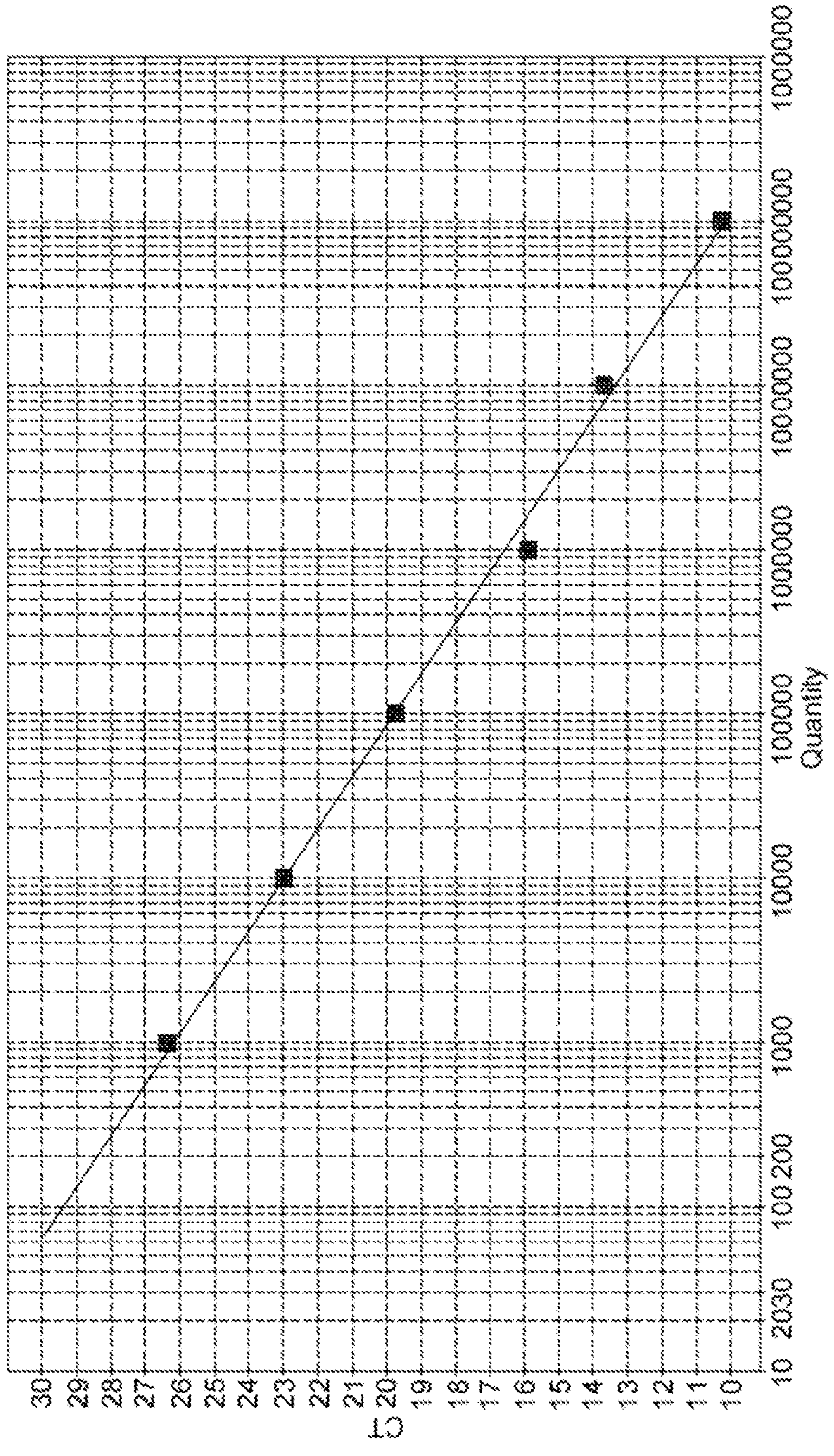
FIG. 1 is a standard curve of TaqMan real-time fluorescence quantitative RT-PCR for HRH4 mRNA.

The present disclosure will be further described below in conjunction with the examples and accompanying drawings.

The present disclosure provides a reagent for detecting an expression level of a human histamine receptor HRH4 mRNA, including a specific primer and a probe for a human histamine receptor HRH4, where the specific primer includes an HRH4-F and an HRH4-R, and the probe includes an H4-Probe; and the HRH4-F has a nucleotide sequence shown in SEQ ID NO. 1, the HRH4-R has a nucleotide sequence shown in SEQ ID NO. 2 and the H4-Probe has a nucleotide sequence shown in SEQ ID NO. 3.

In the present disclosure, the reagent preferably further includes a specific primer and a probe of a reference gene GAPDH; the specific primer of the reference gene GAPDH preferably includes a GAPDH-F and a GAPDH-R, and the probe of the reference gene GAPDH preferably includes a G-Probe; the GAPDH-F preferably has a nucleotide sequence preferably shown in SEQ ID NO. 4, the GAPDH-R preferably has a nucleotide sequence preferably shown in SEQ ID NO. 5 and the G-Probe preferably has a nucleotide sequence preferably shown in SEQ ID NO. 6. 5'-ends of the H4-Probe and G-Probe are separately labeled with different fluorescent reporter groups, and 3'-ends of the H4-Probe and G-Probe are labeled with a same quenching group or different quenching groups. In an example, the fluorescent reporter group preferably includes an FAM and a JOE, and the quenching group includes a BHQ1, and Shanghai Sunny Biotechnology Co., Ltd. is entrusted to synthesize the specific primer and the probe (Table 1).

TABLE 1

TaqMan real-time fluorescence quantitative PCR of primer probe

| Name | Primer sequence (5'-3') | Amplified fragment |
|---|---|---|
| HRH4-F | CTCCATATTCTCTGTTCACAAT (SEQ ID NO: 1) | 128 bp |

TABLE 1-continued

TaqMan real-time fluorescence quantitative PCR of primer probe

| Name | Primer sequence (5'-3') | Amplified fragment |
|---|---|---|
| HRH4-R | TGGATACAAAAGAGGATTGACA (SEQ ID NO: 2) | |
| H4-Probe | (FAM)-AACAGGTCCTAAATC AGTTTGGTA-(BHQ1) (SEQ ID NO: 3) | |
| GAPDH-F | GACAACAGCCTCAAGATCATC (SEQ ID NO: 4) | 70 bp |
| GAPDH-R | CGCCACAGTTTCCCGGAG (SEQ ID NO: 5) | |
| G-Probe | (JOE)-ACTCATGACCACAGT CCATGCCAT-(BHQ1) (SEQ ID NO: 6) | |

In the present disclosure, the HRH4-F, the HRH4-R, the H4-Probe, the GAPDH-F, the GAPDH-R and the G-Probe in the reagent have a concentration or number of moles of 2.25 nM, 1.5 nM, 1.5 nM, 1 nM, 1 nM and 1.5 nM, or respectively.

The present disclosure further provides a kit for one-step detection of an expression level of a human histamine receptor HRH4 mRNA, including the reagent, a PCR reaction solution, an enzyme mixed solution, an ROX reference dye and nuclease-free water.

In the present disclosure, the PCR reaction solution preferably includes a dNTP mix, MgCl and a buffer; the dNTP mix is preferably a mixture of a dATP, a dTTP, a dCTP, and a dGTP, which is purchased from Thermo Fisher Scientific (product number: R0192), and has a working concentration of preferably 0.1-1 mM; the $MgCl_2$ has a concentration of preferably 5-20 mM; and the buffer is a 10-50 mM Tris-HCl buffer (at pH 8.0).

The enzyme mixed solution includes a Taq enzyme, a reverse transcriptase, an RNase inhibitor and a Taq enzyme antibody with a mass ratio of 15:5:4:1 to obtain the best amplification effect.

In the present disclosure, the kit preferably further includes an RNA standard of the human histamine receptor HRH4 to prepare a standard curve.

In the present disclosure, the TaqMan real-time fluorescent quantitative PCR is directly conducted using the RNA as a template without a separate reverse transcription when detecting by the kit; the Taq enzyme is a heat-resistant Taq DNA polymerase, deoxynucleotides in the dNTP are added to a 3-OH terminus one by one using the 3'→5' polymerase activity of the Taq enzyme and using DNA as a template. Meanwhile, mismatched primer ends can be identified and eliminated using the 5'→3' exonuclease activity of the Taq enzyme, which is related to the correction function during the replication, nucleotides can also be hydrolyzed from the 5'-end and mismatched nucleotides can also be excised through several nucleotides. In this way, the chain replacement is realized during the chain extension, and the replaced probe is cut off. The reverse transcriptase can reverse transcribe an mRNA into a cDNA for PCR reaction. The RNase inhibitor is used to suppress the activity of an exogenous RNase. The Taq enzyme antibody is an anti-Taq antibody for hot-start PCR, inhibits DNA polymerase activity after binding to the Taq enzyme, and can effectively suppress the non-specific annealing of primers and the non-specific amplification caused by primer dimers under low temperature. The Taq enzyme antibody is denatured during the initial DNA denaturation of the PCR reaction, and the Taq enzyme recovers the activity to realize PCR amplification.

The present disclosure further provides a method for detecting an expression level of a human histamine receptor HRH4 mRNA in one step based on the reagent or the kit, including the following steps: preparing a reaction system using an RNA standard of the human histamine receptor HRH4 as a template, conducting a qRT-PCR, and constructing a standard curve using a logarithmic value of a copy number as an abscissa and using a Ct value as an ordinate;

preparing a same reaction system using an RNA extracted from a sample as a template, conducting a same qRT-PCR, and determining the expression level of the human histamine receptor HRH4 mRNA using the standard curve.

In the present disclosure, preferably a reaction system is prepared using the reagent or the kit to conduct a qRT-PCR; the reaction system, calculated in 20 μL, preferably includes: 2.4 μL of the nuclease-free water, 10 μL of the PCR reaction solution, 0.5 μL of the enzyme mixed solution, 0.5 μL of the ROX reference dye, 2 μL of the reagent and 5 μL of the standard or the RNA; a qRT-PCR program includes: 42° C. for 30 min; 95° C. for 1 min; 95° C. for 5 s, and 60° C. for 31 s, 40 cycles; and an expression of HRH4 mRNA is calculated according to the standard curve prepared with the standard. The standard curve uses a copy number logarithm as an abscissa (x) and a Ct value as an ordinate (y): $y=-3.177x+34.178$ ($R^2=0.996$). There is no special limitation on the source of the RNA, and the RNA can be extracted from human blood, nasal secretions, bronchial irrigating fluid, saliva or tear samples.

The present disclosure further provides use of the reagent or the kit as a basis in preparing a drug for treating an immune disease or as a tool in dynamically monitoring a therapeutic effect.

In the present disclosure, the immune diseases include preferably allergic diseases. The reagent or the kit can be used to detect the expression level of the histamine H4 receptor (HRH4) mRNA. On one hand, the reagent or kit can determine whether the patient's allergic symptoms are caused by histamine activation of the H4 receptor pathway (since allergic symptoms caused by non-histamine pathways do not express histamine receptors) and guide the dosage (since higher H4 receptor expression level requires higher dosage of H4 receptor antagonist). On the other hand, the effect of H4 receptor antagonist therapy can be dynamically monitored. The use of the present disclosure is preferably the same as that described above, and will not be repeated here.

The reagent for detecting an expression level of a human histamine receptor HRH4 mRNA, the kit and the detection method provided by the present disclosure are described in detail below with reference to the examples, but these examples should not be understood as limiting the claimed protection scope of the present disclosure.

Unless otherwise specified, the test materials involved in the present disclosure are all commercially-available conventional in the art:

a whole-blood total RNA kit (Hangzhou Simgen Biological Reagent Development Co., Ltd., product number: 5201050);

a HiScribe T7 High Yield RNA Synthesis Kit (New England Biolabs, product number: E2050S);

- an Applied Biosystems™ 7300 fluorescence quantitative PCR instrument (Thermo Fisher Scientific, USA);
- a −80° C. low-temperature refrigerator (Thermo Fisher Scientific, USA);
- a high-speed and low-temperature table centrifuge (Eppendorf, Germany); and
- a Qubit 3 fluorometer (Thermo Fisher Scientific, USA).

Example 1

1. Shanghai Sunny Biotechnology Co., Ltd. was entrusted to synthesize the primers and probes shown in Table 1.

2. Preparation of a Standard

Figure 8:
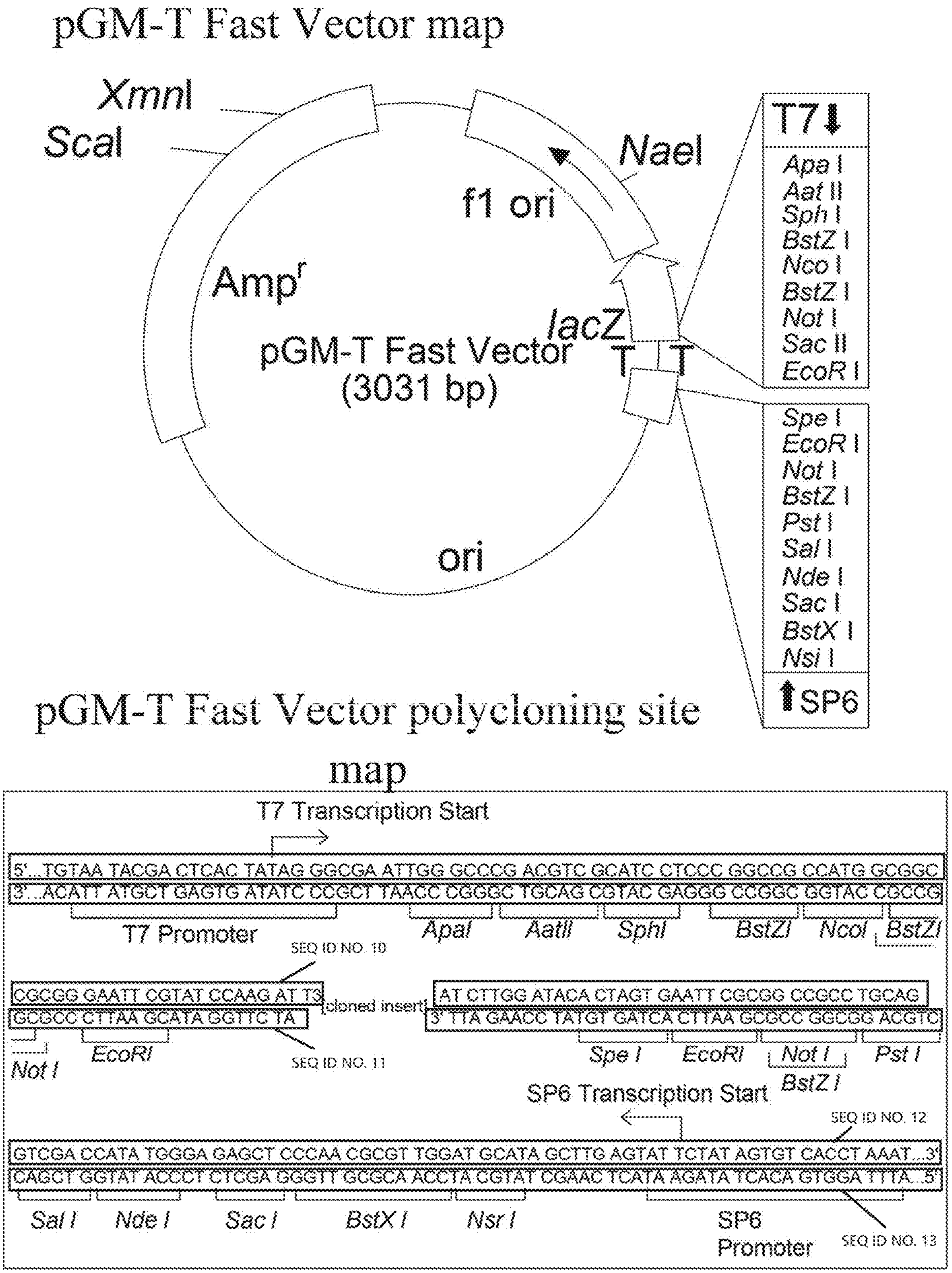
FIG. 8 is a plasmid structure map of pGM-T vector, wherein the pGM-T Fast Vector polycloning site map shows a nucleotide sequence numbered SEQ ID NO. 10 (TGTAATACGACTCACTATAGGGCGAATTGGGCCCGACGTCGCATCCTCCC GGCCGCCATGGCGGCCGCGGGAATTCGTATCCAAGATT), a nucleotide sequence numbered SEQ ID NO. 11 (ATCTTGGATACGAATTCCCGCGGCCGCCATGGCGGCCGGGAGCATGCGAC GTCGGGCCCAATTCGCCCTATAGTGAGTCGTATTACA), a nucleotide sequence numbered SEQ ID NO. 12 (ATCTTGGATACACTAGTGAATTCGCGGCCGCCTGCAGGTCGACCATATGG GAGAGCTCCCAACGCGTTGGATGCATAGCTTGAGTATTCTATAGTGTCACCTAAAT), and a nucleotide sequence numbered SEQ ID NO. 13 (ATTTAGGTGACACTATAGAATACTCAAGCTATGCATCCAACGCGTTGGGA GCTCTCCCATATGGTCGACCTGCAGGCGGCCGCGAATTCACTAGTGTATCCAAGATT).

In-vitro transcription: a pGM-T ligation kit [TIANGEN Biotech (Beijing) Co., Ltd., product number: VT202-01] was used, a HRH4 plasmid DNA (constructed and synthesized by entrusting Nanjing GenScript Biotech Co., Ltd., FIG. 8) was constructed using a pGM-T as a vector, and the HRH4 plasmid DNA was transcribed into an mRNA in vitro using a HiScribe T7 High Yield RNA Synthesis Kit (NEW ENGLAND BioLabs, product number: E2040S).

An initial copy number of the RNA was calculated according to a copy number calculation formula: copy number=[$6.02\times10^{23}\times$RNA concentration (ng/μL)$\times10^{-9}$]/[RNA length (bp)×340]. The HRH4 mRNA was diluted with nuclease-free water to $1.0\times10^{10}$ copies/μL to obtain a HRH4 mRNA standard.

3. Extraction and Dilution of Whole-Blood RNA

Whole-blood total RNA was extracted from ethylenediaminetetraacetic acid (EDTA) anticoagulated whole-blood samples with the whole-blood total RNA kit, quantificated with the Qubit 3 fluorometer, and diluted with the nuclease-free water to 20 ng/μL.

4. TaqMan Real-Time Fluorescent Quantitative PCR

A 20 μL system was prepared using the standard/whole-blood RNA as a template with: 2.4 μL of the nuclease-free water, 10 μL of the PCR reaction solution, 0.5 μL of the enzyme mixed solution, 0.5 μL of the ROX reference dye, 2 μL of a mixed solution of the primer and the probe, and 5 μL of the standard or the RNA.

A qRT-PCR program was as follow: 42° C. for 30 min; 95° C. for 1 min; 95° C. for 5 s, and 60° C. for 31 s, 40 cycles.

A detection fluorescein was set up: FAM, JOE; a reference fluorescence was: ROX; the reaction system was: 20 μL; and a fluorescence signal collection was: 60° C. for 31 sec.

5. Generation of a Standard Curve

The HRH4 standard was diluted in a 10-fold gradient using $1.0\times10^{8}$-$1.0\times10^{3}$ copies/μl as a template, 3 replicates were conducted for each dilution, and TaqMan real-time fluorescence quantitative RT-PCR detection was conducted to generate the standard curve.

The result is shown in FIG. 1. A copy number logarithm is taken as an abscissa and a Ct value is taken as an ordinate, and a regression equation is obtained: $y=-3.177x+34.178$ ($R^2=0.996$), indicating the copy number logarithm of a standard equation has very high correlation with the Ct value.

6. Precision Detection $1.0\times10^{7}$ copies/μL and $1.0\times10^{4}$ copies/μL of standards were taken as templates, 10 replicates were conducted for each concentration; 10 times of TaqMan real-time fluorescent quantitative RT-PCR detections were conducted, the coefficient of variation of the logarithm of each concentration was calculated, respectively; and statistical analysis was conducted to analyze the precision of the detection method.

Figure 2:
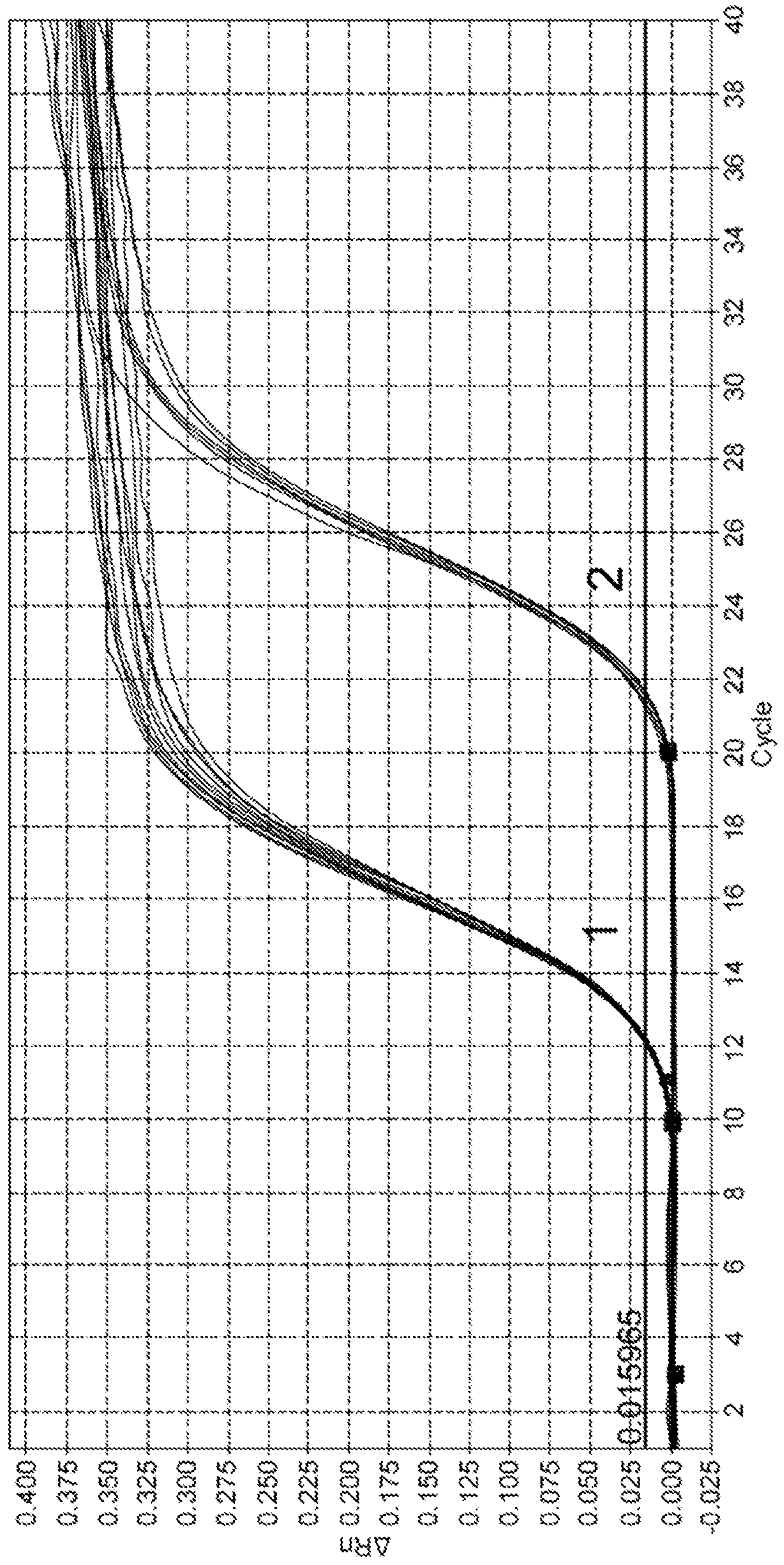
FIG. 2 is a result of precision detection, where 1:$1.0\times10^7$ copies/μL, and 2:$1.0\times10^4$ copies/μL.

The results are shown in Table 2 and FIG. 2. The coefficient of variation of the logarithm of each concentration is 0.443% and 0.430% separately, which are less than 5%, indicating that the TaqMan real-time fluorescent quantitative RT-PCR detection method established by the present disclosure has excellent precision.

TABLE 2

Precision detection result

| Theoretical copy number | Mean logarithm of copy number | SD | C.V |
|---|---|---|---|
| $1.0\times10^{7}$ | 6.907 | 0.031 | 0.443% |
| $1.0\times10^{4}$ | 3.988 | 0.017 | 0.430% |

7. Accuracy Detection

Figure 3:
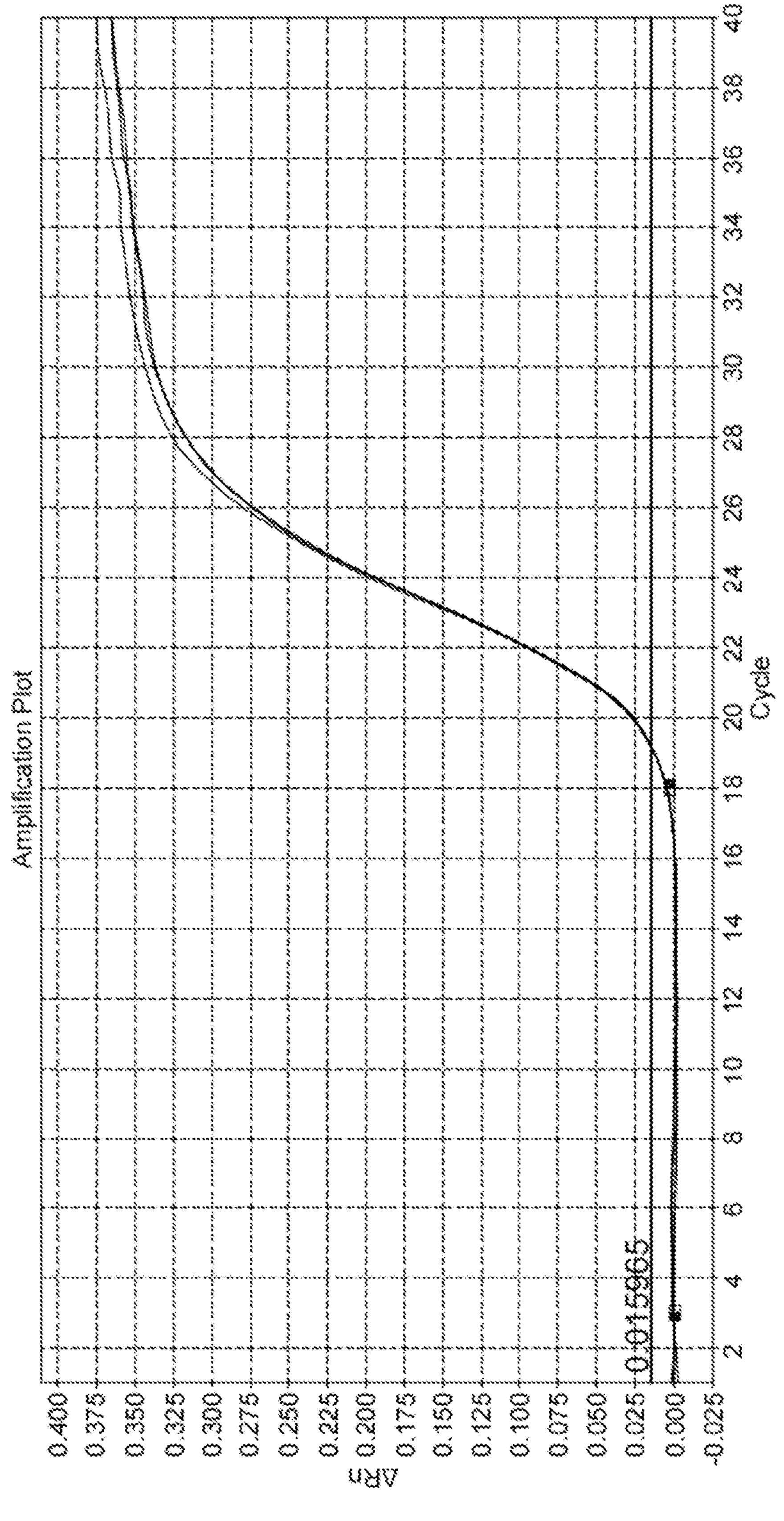
FIG. 3 is a result of accuracy detection.

A $1.0\times10^{6}$ copies/μL of standard was subjected to 30-fold dilution (2 μL $1.0\times10^{6}$ copies/μL of a standard+58 μL of nuclease-free water) as a template, for 3 replicates; 3 times of TaqMan real-time fluorescence quantitative RT-PCR detections were conducted, and the absolute deviation of the logarithm of each concentration was calculated. The results are shown in FIG. 3. The absolute deviation of the logarithm of each concentration is 0.126, 0.137, and 0.131, respectively, within the range of ±0.5, indicating that the TaqMan real-time fluorescent quantitative RT-PCR detection method established by the present disclosure has excellent accuracy.

TABLE 3

Accuracy detection data

| $C_T$ | Results (copies/μL) | Copy number logarithm | Theoretical copy number (copies/μL) | Theoretical copy number logarithm | Absolute deviation |
|---|---|---|---|---|---|
| 19.409 | $4.454\times10^{4}$ | 4.649 | $3.333\times10^{4}$ | 4.523 | 0.126 |
| 19.373 | $4.570\times10^{4}$ | 4.660 | | | 0.137 |
| 19.393 | $4.505\times10^{4}$ | 4.654 | | | 0.131 |

8. Sensitivity Detection

A 10.0 copies/μL of standard was taken as a template, for 25 replicates, 25 times of TaqMan real-time fluorescence quantitative RT-PCR detection were conducted to check whether there were amplifications, and the sensitivity of the detection method was analyzed.

Figure 4:
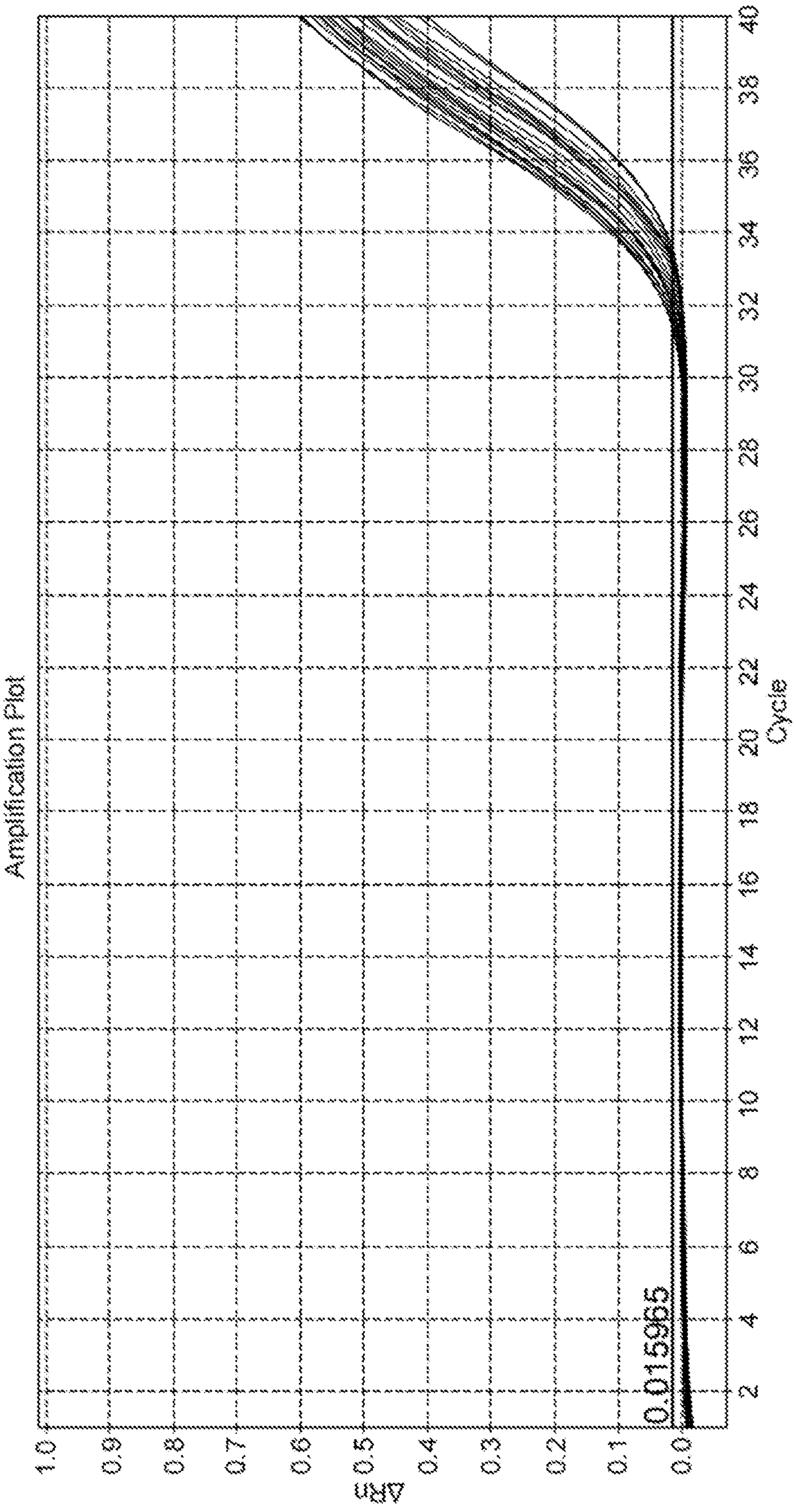
FIG. 4 is a result of sensitivity detection.

The results are shown in Table 4 and FIG. 4. A total of 25 detection results are obtained, reaching 100%. This indicates that the TaqMan real-time fluorescent quantitative RT-PCR detection method established by the present disclosure has very high sensitivity, and the minimum number of detected copies is less than 10 copies/μL.

TABLE 4

Ct value results of sensitivity detection

| | | | | |
|---|---|---|---|---|
| 32.533 | 32.716 | 33.514 | 32.321 | 31.944 |
| 32.110 | 31.967 | 33.336 | 33.215 | 31.506 |
| 31.673 | 33.513 | 32.747 | 31.747 | 31.961 |
| 31.605 | 32.968 | 33.157 | 31.965 | 32.189 |
| 32.769 | 32.178 | 32.692 | 32.465 | 31.669 |

9. Clinical Sample Detection

Whole-blood samples of patients and normal persons were taken to extract and dilute whole-blood RNA according to the above steps, and TaqMan real-time fluorescent quantitative RT-PCR detection was conducted according to the above steps.

Figure 5:
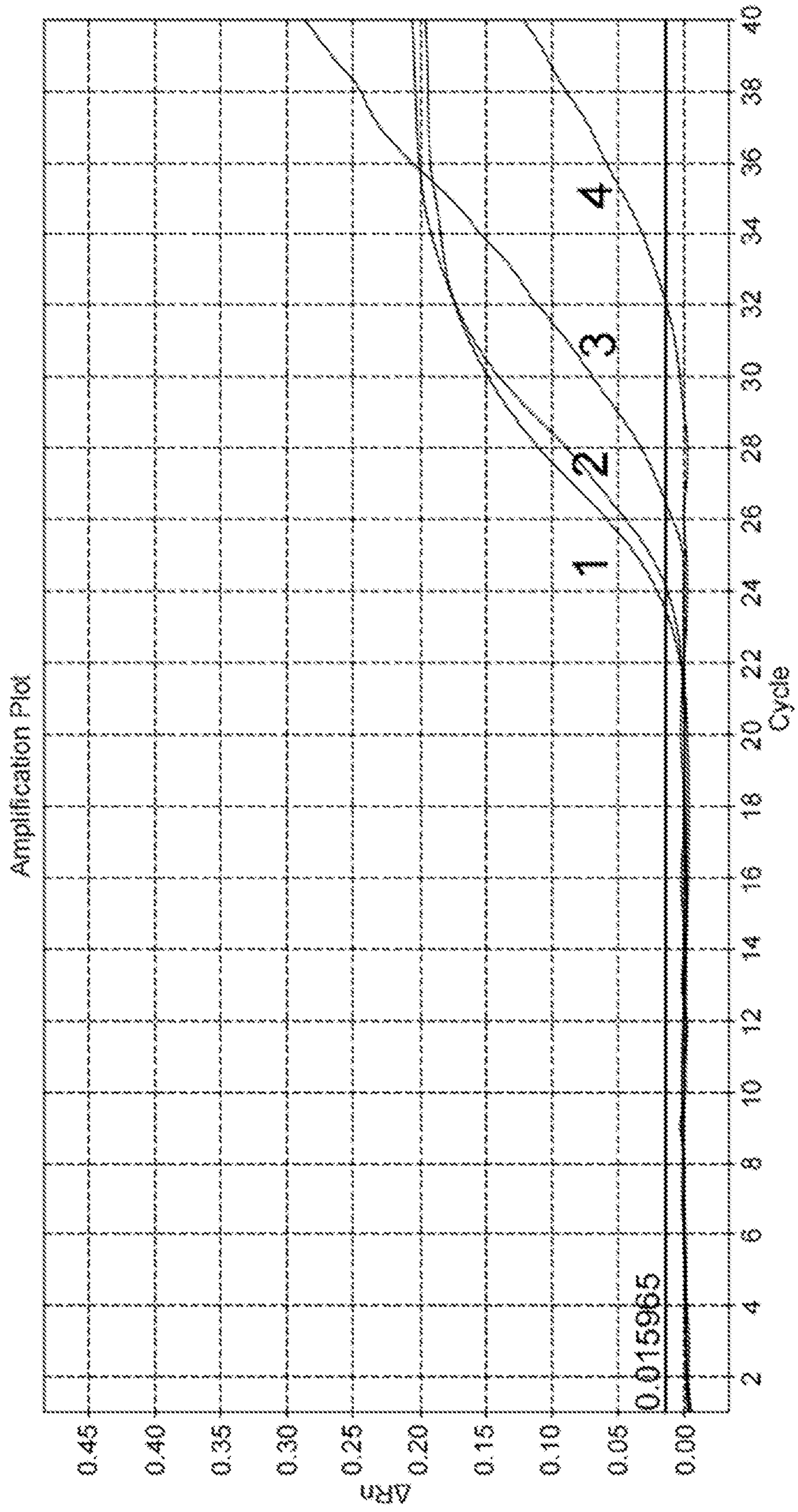
FIG. 5 is a result of clinical sample detection, where 1: Case 3 GAPDH mRNA before treatment; 2: Case 3 GAPDH mRNA after treatment; 3: Case 3 HRH4 mRNA before treatment; 4: Case 3 HRH4 mRNA after treatment.

Compared with a domestic brand of histamine H4 receptor (HRH4) kit of enzyme-linked immunosorbent assay (ELISA), the results are shown in Table 5 and FIG. 5. The TaqMan real-time fluorescent quantitative RT-PCR detection method established in the present disclosure has better sensitivity and specificity than that of a counterpart reagent, and can effectively monitor the treatment effect.

TABLE 5

Comparison of clinical sample detection effect

| | | Product of the present disclosure | | Histamine H4 receptor (HRH4) kit of ELISA | |
|---|---|---|---|---|---|
| SN | Sample type | Results (copies/μL) | positive/ negative | Result (ng/mL) | positive/ negative |
| 1 | Case 1 before treatment | 1154.669 | + | 678.3 | + |
| 2 | Case 1 after treatment | 960.673 | + | 153.2 | + |
| 3 | Case 2 before treatment | 911.955 | + | 487.3 | + |
| 4 | Case 2 after treatment | 496.380 | − | 37.6 | − |
| 5 | Case 3 before treatment | 1620.624 | + | 781.4 | + |
| 6 | Case 3 after treatment | 32.378 | − | 147.6 | + |
| 7 | Case 4 | 1447.242 | + | 539.1 | + |
| 8 | Healthy control 1 | 756.543 | − | 356.4 | + |
| 9 | Healthy control 2 | 30.457 | − | 19.2 | − |
| 10 | Healthy control 3 | 61.125 | − | 28.7 | − |

Figure 6:
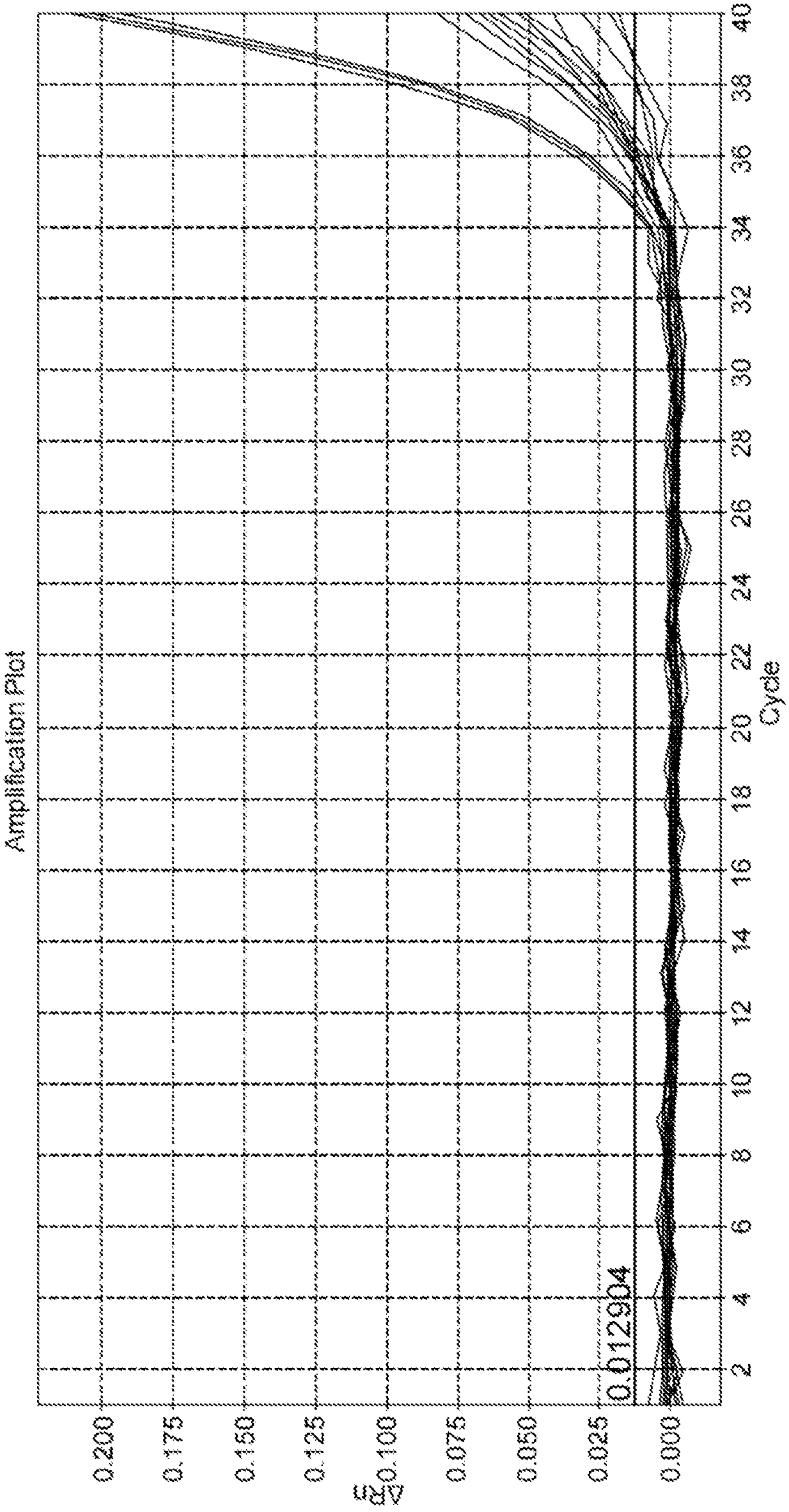
FIG. 6 is a low-precision amplification curve in the case of non-optimal primer and probe designs.

Comparative Example 1 Results of Amplification Using Other Non-Optimal Primers and Probes The primers and probes in the system used in the present disclosure in Example 5 were replaced with other non-optimal primers and probes. The results are shown in FIG. 6. When using non-optimal HRH4 primers and probes, the amplification results of the standard curve are poor, with almost no amplification.

Non-optimal HRH4 primers and probes were as follows:

```
HRH4-F (SEQ ID NO. 7):
GCCAGATACTAATAGCACAAT;

HRH4-R (SEQ ID NO. 8):
CCACAAAAGCTAAAATGACCAA;
and

H4-Probe (SEQ ID NO. 9):
(FAM)-AAGCACTCGTGTTACTTTAGCA-(BHQ1).
```

Comparative Example 2 Comparison of the Effect of Enzyme Mixed Solution

Figure 7A:
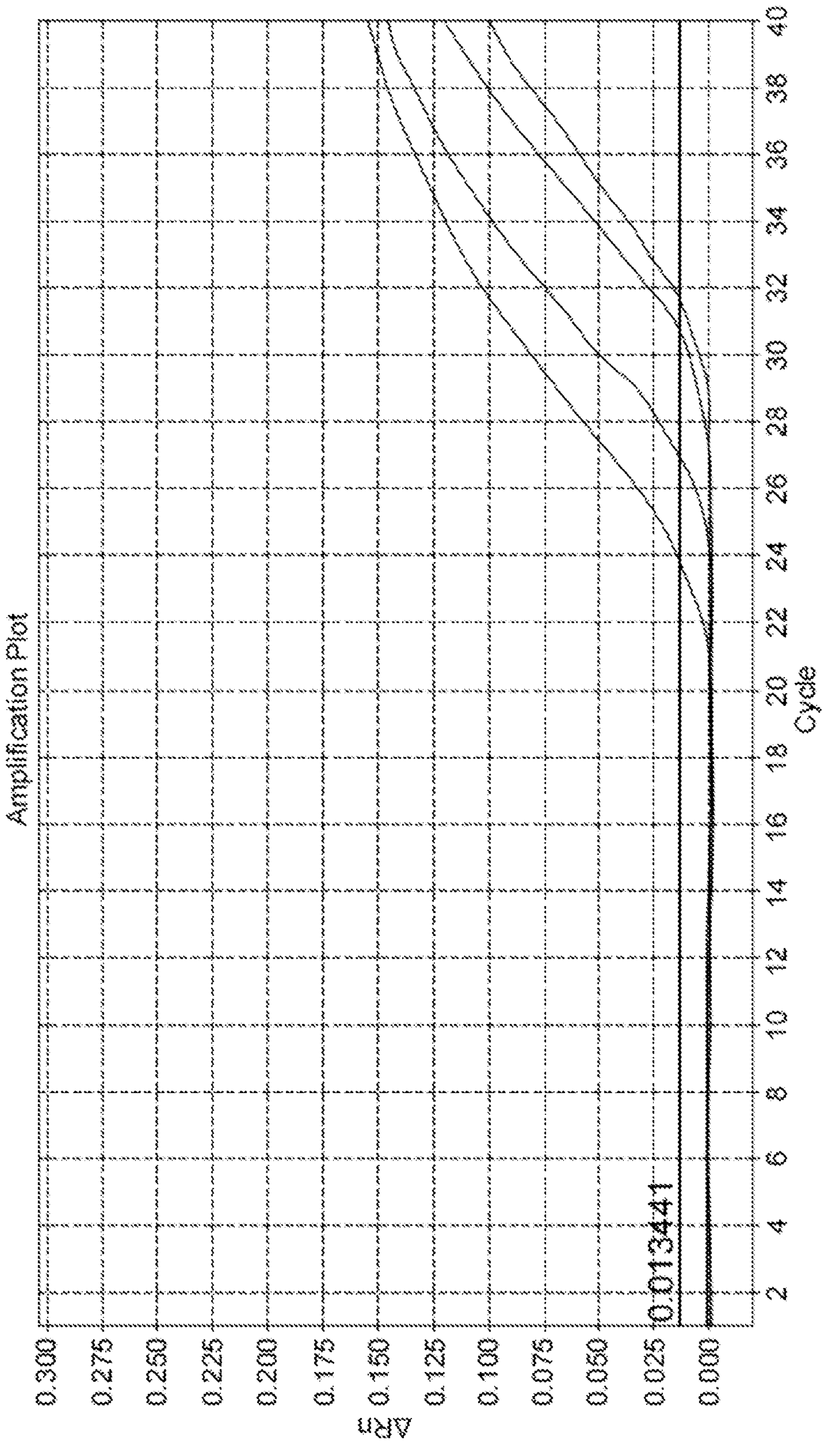
FIGS. 7A and 7B are effect of the enzyme mixed solution on amplification.
Figure 7B:
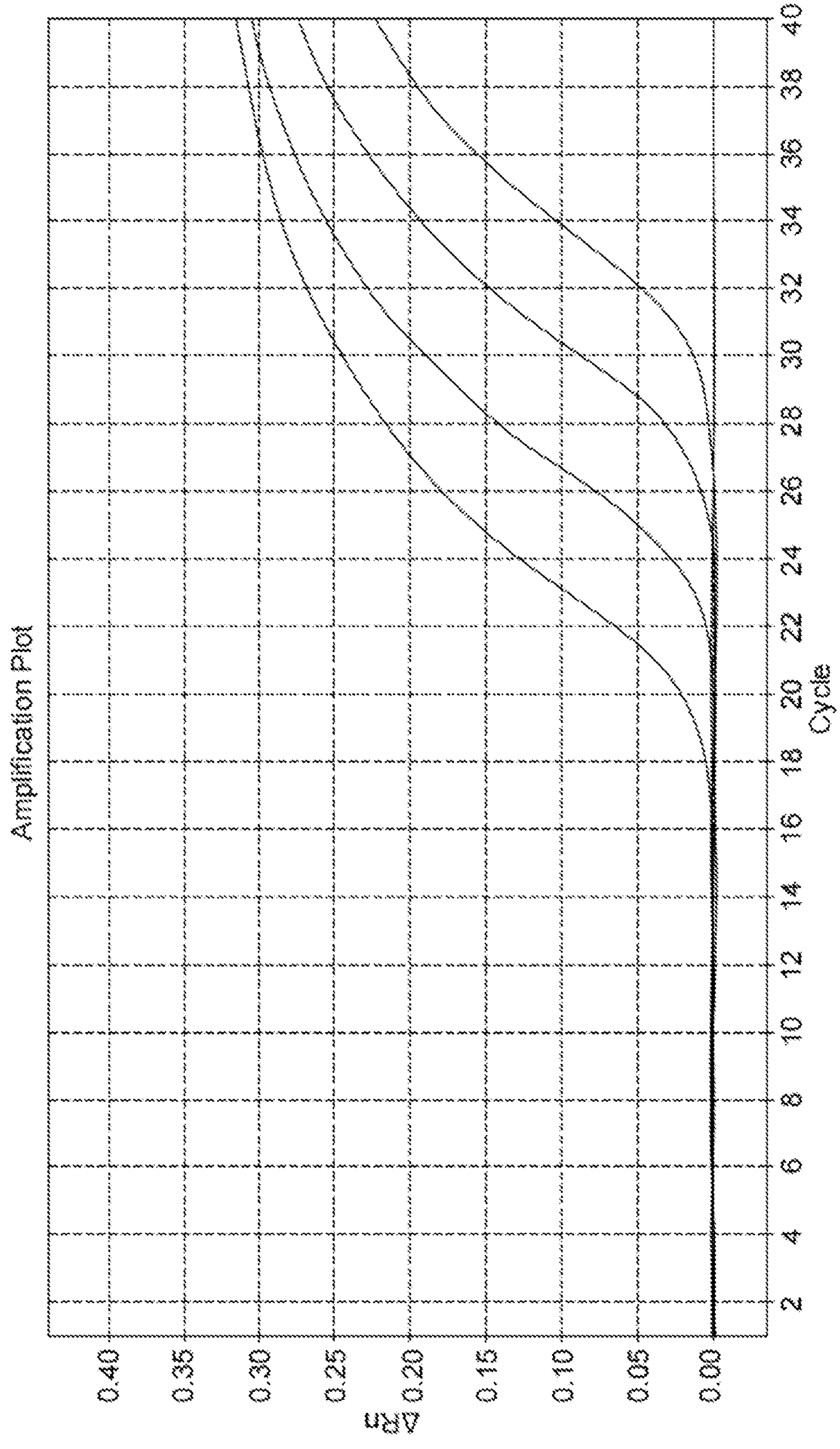

An amplification was conducted using a non-optimal ratio of enzyme mixed solution (the Taq enzyme, reverse transcriptase, RNase inhibitor and Taq enzyme antibody had a mass ratio of 16:3:5:1) and a best ratio of enzyme mixed solution on 4 gradients $1.0\times10^3$-$1.0\times10^6$ copies/μl on a calibration curve. An amplification result using the non-optimal ratio of enzyme mixed solution is shown in FIG. 7A, and an amplification result using the best ratio of enzyme mixed solution is shown in FIG. 7B. It can be seen that the best enzyme mixed solution has a desirable amplification effect.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A reagent for detecting an expression level of a human histamine receptor H4 (HRH4) messenger ribonucleic acid (mRNA), comprising a primer pair and a probe for human histamine receptor HRH4, wherein the primer pair comprises an HRH4-F and an HRH4-R primer, and the probe comprises an H4-Probe;

Wherein the HRH4-F primer comprises SEQ ID NO. 1, the HRH4-R primer comprises SEQ ID NO. 2 and the H4-Probe comprises SEQ ID NO. 3, wherein the 5'-end of the H4-Probe is labeled with a fluorescent reporter group comprising a 6-carboxyfluorescein (FAM) or a 2,7-dimethyl-4,5-dichloro-6-carboxyfluorescein (JOE), the 3'-end of the H4-Probe is labeled with a quenching group comprising a Black Hole Quencher-1 (BHQ1); and the HRH4-F, the HRH4-R, and the H4-Probe in the reagent have a concentration of 2.25 nM, 1.5 nM, and 1.5 nM, respectively.

2. The reagent according to claim 1, further comprising a primer pair and a probe of a reference gene glyceraldehyde-3-phosphate dehydrogenase (GAPDH), wherein the primer pair for the reference gene GAPDH comprises a GAPDH-F and a GAPDH-R primer, and the probe of the reference gene GAPDH comprises a G-Probe;

Wherein the GAPDH-F primer comprises SEQ ID NO. 4, the GAPDH-R comprises SEQ ID NO. 5 and the G-Probe comprises SEQ ID NO. ID NO. 6, wherein 5'-end of the G-Probe is labeled with a fluorescent reporter group comprising a 6-carboxyfluorescein (FAM) or a 2,7-dimethyl-4,5-dichloro-6-carboxyfluorescein (JOE), 3'-end of the G-Probe is labeled with a quenching group comprising a Black Hole Quencher-1 (BHQ1); and the 5'-ends of the H4-Probe and G-Probe are separately labeled with different fluorescent reporter groups, and 3'-ends of the H4-Probe and G-Probe are labeled with a same quenching group.

3. The reagent according to claim 2, wherein the GAPDH-F, the GAPDH-R and the G-Probe in the reagent have a concentration of 1 nM, 1 nM, and 1.5 nM, respectively.

4. A kit for one-step detection of an expression level of a human histamine receptor H4 (HRH4) messenger ribonucleic acid (mRNA), comprising the reagent according to claim 1, a polymerase chain reaction (PCR) reaction solution, an enzyme mixed solution, a carboxy-X-rhodamine (ROX) reference dye and nuclease-free water.

5. The kit according to claim 4, further comprising a primer pair and a probe of a reference gene glyceraldehyde-3-phosphate dehydrogenase (GAPDH), wherein the primer pair of the reference gene GAPDH comprises a GAPDH-F and a GAPDH-R primer, and the probe of the reference gene GAPDH comprises a G-Probe;

wherein the GAPDH-F primer comprises SEQ ID NO. 4, the GAPDH-R primer comprises SEQ ID NO. 5 and the G-Probe comprises SEQ ID NO. ID NO. 6.

6. The kit according to claim 4, wherein 5'-ends of the H4-Probe and a G-Probe are separately labeled with different fluorescent reporter groups, and 3'-ends of the H4-Probe and the G-Probe are labeled with a same quenching group.

7. The kit according to claim 5, wherein the HRH4-F, the HRH4-R, the H4-Probe, the GAPDH-F, the GAPDH-R, and the G-Probe in the reagent have a concentration of 2.25 nM, 1.5 nM, 1.5 nM, 1 nM, 1 nM, and 1.5 nM, respectively.

8. The kit according to claim 4, wherein the PCR reaction solution comprises a deoxy-ribonucleoside triphosphate (dNTP) mix, MgCl2 and a buffer; and the enzyme mixed solution comprises a *Thermus aquaticus* (Taq) enzyme, a reverse transcriptase, a ribonuclease (RNase) inhibitor and a Taq enzyme antibody with a mass ratio of 15:5:4:1.

* * * * *

SEQUENCE LISTING

```
<160> NUMBER OF SEQ ID NOS: 13

<210> SEQ ID NO 1
<211> LENGTH: 22
<212> TYPE: DNA
<213> ORGANISM: artificial sequence
<220> FEATURE:
<223> OTHER INFORMATION: primer: HRH4-F

<400> SEQUENCE: 1

ctccatattc tctgttcaca at                                              22


<210> SEQ ID NO 2
<211> LENGTH: 22
<212> TYPE: DNA
<213> ORGANISM: artificial sequence
<220> FEATURE:
<223> OTHER INFORMATION: primer: HRH4-R

<400> SEQUENCE: 2

tggatacaaa agaggattga ca                                              22


<210> SEQ ID NO 3
<211> LENGTH: 24
<212> TYPE: DNA
<213> ORGANISM: artificial sequence
<220> FEATURE:
```

<223> OTHER INFORMATION: H4-Probe

<400> SEQUENCE: 3
aacaggtcct aaatcagttt ggta 24

<210> SEQ ID NO 4
<211> LENGTH: 21
<212> TYPE: DNA
<213> ORGANISM: artificial sequence
<220> FEATURE:
<223> OTHER INFORMATION: primer: GAPDH-F

<400> SEQUENCE: 4
gacaacagcc tcaagatcat c 21

<210> SEQ ID NO 5
<211> LENGTH: 18
<212> TYPE: DNA
<213> ORGANISM: artificial sequence
<220> FEATURE:
<223> OTHER INFORMATION: primer: GAPDH-R

<400> SEQUENCE: 5
cgccacagtt tcccggag 18

<210> SEQ ID NO 6
<211> LENGTH: 24
<212> TYPE: DNA
<213> ORGANISM: artificial sequence
<220> FEATURE:
<223> OTHER INFORMATION: G-Probe

<400> SEQUENCE: 6
actcatgacc acagtccatg ccat 24

<210> SEQ ID NO 7
<211> LENGTH: 21
<212> TYPE: DNA
<213> ORGANISM: artificial sequence
<220> FEATURE:
<223> OTHER INFORMATION: primer: HRH4-F

<400> SEQUENCE: 7
gccagatact aatagcacaa t 21

<210> SEQ ID NO 8
<211> LENGTH: 22
<212> TYPE: DNA
<213> ORGANISM: artificial sequence
<220> FEATURE:
<223> OTHER INFORMATION: primer: HRH4-R

<400> SEQUENCE: 8
ccacaaaagc taaaatgacc aa 22

<210> SEQ ID NO 9
<211> LENGTH: 22
<212> TYPE: DNA
<213> ORGANISM: artificial sequence
<220> FEATURE:
<223> OTHER INFORMATION: H4-Probe

<400> SEQUENCE: 9
aagcactcgt gttactttag ca 22

-continued

```
<210> SEQ ID NO 10
<211> LENGTH: 88
<212> TYPE: DNA
<213> ORGANISM: artificial Sequence
<220> FEATURE:
<223> OTHER INFORMATION: pGM-T fragment

<400> SEQUENCE: 10

tgtaatacga ctcactatag ggcgaattgg gcccgacgtc gcatcctccc ggccgccatg     60

gcggccgcgg gaattcgtat ccaagatt                                        88


<210> SEQ ID NO 11
<211> LENGTH: 87
<212> TYPE: DNA
<213> ORGANISM: artificial Sequence
<220> FEATURE:
<223> OTHER INFORMATION: pGM-T fragment

<400> SEQUENCE: 11

atcttggata cgaattcccg cggccgccat ggcggccggg agcatgcgac gtcgggccca     60

attcgcccta tagtgagtcg tattaca                                         87


<210> SEQ ID NO 12
<211> LENGTH: 106
<212> TYPE: DNA
<213> ORGANISM: artificial Sequence
<220> FEATURE:
<223> OTHER INFORMATION: pGM-T fragment

<400> SEQUENCE: 12

atcttggata cactagtgaa ttcgcggccg cctgcaggtc gaccatatgg gagagctccc     60

aacgcgttgg atgcatagct tgagtattct atagtgtcac ctaaat                   106


<210> SEQ ID NO 13
<211> LENGTH: 107
<212> TYPE: DNA
<213> ORGANISM: artificial Sequence
<220> FEATURE:
<223> OTHER INFORMATION: pGM-T fragment

<400> SEQUENCE: 13

atttaggtga cactatagaa tactcaagct atgcatccaa cgcgttggga gctctcccat     60

atggtcgacc tgcaggcggc cgcgaattca ctagtgtatc caagatt                  107
```